United States Patent
Duffy et al.

(10) Patent No.: US 7,194,359 B2
(45) Date of Patent: Mar. 20, 2007

(54) ESTIMATING THE ACCURACY OF MOLECULAR PROPERTY MODELS AND PREDICTIONS

(75) Inventors: Nigel P. Duffy, San Francisco, CA (US); Guido Lanza, San Francisco, CA (US); Jessen Yu, San Francisco, CA (US)

(73) Assignee: Pharmix Corporation, Brisbane, CA (US)

( * ) Notice: Subject to any disclaimer, the term of this patent is extended or adjusted under 35 U.S.C. 154(b) by 49 days.

(21) Appl. No.: 11/172,216

(22) Filed: Jun. 29, 2005

(65) Prior Publication Data

US 2005/0288871 A1 Dec. 29, 2005

Related U.S. Application Data

(60) Provisional application No. 60/584,820, filed on Jun. 29, 2004, provisional application No. 60/584,819, filed on Jun. 29, 2004.

(51) Int. Cl.
G01N 1/30 (2006.01)
(52) U.S. Cl. ...................................... 702/27; 435/40.5
(58) Field of Classification Search ................. 702/27, 702/28–30; 435/40.5
See application file for complete search history.

(56) References Cited

U.S. PATENT DOCUMENTS 5,446,681 A * 8/1995 Gethner et al. ............... 702/27

6,081,766 A 6/2000 Chapman et al.
2002/0123848 A1 9/2002 Schneiderman et al.
2005/0278124 A1 12/2005 Duffy et al.

FOREIGN PATENT DOCUMENTS

WO WO-03040994 A2 5/2003
WO WO-03040994 A3 5/2003

OTHER PUBLICATIONS

"International Search Report, PCT/US2005/023434", 1-15.
Anthony, M., et al., "A Result of Vapnik with Applications", *Department of Statistical and Mathematical Sciences* (Nov. 23, 1991), 1-13.
Bartlett, P. L., et al., "Rademacher and Gaussian Complexities: Risk Bounds and Structural Results", *Journal of Machine Learning Research*, 3 (2002), 463-482.
Beck, B., et al., "QM/NN QSPR Models with Error Estimation: Vapor Pressure and LogP", *J. Chem. Inf. Comput. Sci.*, 40 (4), American Chemical Society (Jul. 2000), 1046-1051.
Benigni, R., et al., "The Second National Toxicology Program Comparative Exercise on the Prediction of Rodent Carcinogenicity: Definitive Results", *Mutation Research*, 566 (1), www.sciencedirect.com (Jan. 2004), 49-63.

(Continued)

*Primary Examiner*—Edward Raymond
(74) *Attorney, Agent, or Firm*—Moser IP Law Group

(57) ABSTRACT

Embodiments of the invention provide methods for evaluating the accuracy of a molecular model properties model (or predictions generated using a molecular properties model). The accuracy of a molecular properties model may be evaluated using three general approaches, (i) by using the same data set to both train the model and to estimate the accuracy of the model, (ii) by using distinct data sets to train and subsequently test a model, and (iii) by using multiple models (or sets of predictions).

33 Claims, 4 Drawing Sheets

OTHER PUBLICATIONS

Boucheron, S., et al., "Concentration Inequalities", 215-247.

Carlsen, L., et al., "Partial order ranking-based QSAR's: Estimation of Solubilities and Octanol-Water Partitioning", *Chemosphere*, 43 (2001), 295-302.

Cuissart, B., et al., "The Maximum Common Substructure as a Molecular Depiction in a Supervised Classification Context: Experiments in Quantitative Structure/Biodegradability Relationships", *J.Chem. Inf. Comput. Science*, 42 (5), American Chemical Society (2002), 1043-1052.

Farkas, O., et al., "Quantitative Structure—Antioxidant Activity Relationships of Flavonoid Compounds", *Molecules*, 9, http://www.mdpi.org(2004), 1079-1088.

Hawkins, D. M., et al., "QSAR with Few Compounds and Many Features", *Journal of Chem. Inf. Comput. Science*, 41(3) (2001), 663-670.

Hawkins, D. M., et al., "QSARs for Chemical Mutagens from Structure: Ridge Regression Fitting and Diagnostics", *Environmental Toxicology and Pharmacology* 16 (1-2), www.sciencedirect.com (Mar. 2004), 37-44.

Rosset, S., "Model Selection via the AUC", *Proceedings of the 21st International Conference on Machine Learning* (2004), 8 pgs.

Shawe-Taylor, J., et al., "Structural Risk Minimization over Data-Dependent Hierarchies" (Feb. 24, 1998), 1-35.

Takaoka, Y., et al., "Development of a Method for Evaluating Drug-Likeness and Ease of Synthesis Using a Data Set in Which Compounds are Assigned Scores Based on Chemists' Intuition", *J. Chem. Inf. Comput. Sci.*, 43, American Chemical Society (2003), pp. 1269-1275.

Taskinen, J., et al., "Prediction of Physicochemical Properties Based on Neural Network Modelling", *Advanced Drug Delivery Reviews*, 55 (9), www.sciencedirect.com (Sep. 12, 2003), 1163-1183.

Vapnik, V., et al., "Measuring the VC-dimension of a Learning Machine", *Neural Computation* (1994), 1-22.

Votano, J. R., et al., "Three New Consensus QSAR Models for the Prediciton of Ames Genotoxicity", *Mutagenesis* (2004), 1-12.

Wang, Z., et al., "Particle Swarm Optimization and Neural Network Application for QSAR", 1-8.

Wieschaus, E. E., et al., "A Comparison of Methods for the Reduction of Attributes Before Classification in Data Mining", (Dec. 2003), 1-16.

"Equbits." *LIMSFinder*. <http://www.limsfinder.com/community/blog_detail.phd?id=1553_0_2_0_C75>.

Platt et al. "QSAR in Grossly Underdetermined Systems: Opportunities and Issues." *IBM J. Res.& Dev*, May/Jul. 2001 vol. 45(3/4): pp. 533-544.

Ekins et al. "Three- and Four-Dimensional Quantitative Structure Activity Relationship Analyses of Cytochrome P-450 3A4 Inhibitors." *Pharmacology and Experimental Therapeutics*. Jul. 1999 vol. 290(1): pp. 429-438.

Von Korff et al. "Validation of Variable Selection Techniques: Applications to QSAR." Institut für Pharmazie und Lebensmittelchemie. <http://www.pharmazie.uni-wuerzburg.de/AKBaumann/reports/qsar2002_2a3b.pdf>.

\* cited by examiner

ESTIMATING THE ACCURACY OF MOLECULAR PROPERTY MODELS AND PREDICTIONS

CROSS-REFERENCE TO RELATED APPLICATIONS

This application claims priority to U.S. provisional patent application Ser. No. 60/584,820, filed Jun. 29, 2004, and to U.S. Provisional patent application Ser. No. 60/584,819, filed Jun. 29, 2004, both of which are incorporated by reference herein in their entirety.

This application is also related to the following: (1) U.S. Pat. No. 6,571,226, Issued May 23, 2003, (2) U.S. patent application Ser. No. 11/074,587, filed on Mar. 8, 2005, and (3) U.S. patent application Ser. No. 11,172,215, filed on even date herewith entitled "Molecular Property Modeling Using Ranking". Each of the aforementioned patent and applications are herein incorporated by reference in their entirety.

BACKGROUND OF THE INVENTION

1. Field of the Invention

Embodiments of the present invention generally relate to machine learning techniques and computational chemistry. More particularly, embodiments of the invention relate to techniques for estimating the accuracy of a molecular properties model, and for estimating the accuracy of predictions generated by a molecular properties model.

2. Description of the Related Art

Many industries use machine learning techniques to construct software applications that provide a predictive model of relevant phenomena. For example, machine learning applications have been developed to detect fraudulent credit card transactions, predict creditworthiness, or recognize words spoken by an individual. Machine learning techniques have also been applied to create predictive models of chemical and biological systems. Generally, machine learning techniques are used to construct a software application that improves its ability to perform a task as it attribute or quantity from known information (e.g., whether a particular molecule will bind to a protein receptor, based on an evaluation of other molecules known to, or to not, bind to the protein) or to classify an object as belonging to a particular group or class. A machine learning application may improve its performance on the selected task as the number of training examples used to train the model is increased. Each training example may include an example of an object (e.g., a molecule, compound, or substituent group thereof), along with a value for the otherwise unknown classification of the object.

During "training" a selected machine learning algorithm processes thousands, if not millions or billions, of potential models (also referred to as hypotheses). By evaluating how well different possible potential models perform against the training data a trained model is selected. For example, a classification learning algorithm may be configured to process a set of training examples that includes both an object and a classification for the object. In one embodiment, the hypothesis that correctly classifies the greatest number of training examples may be selected by a machine learning algorithm as the molecular properties model. Further, various machine learning algorithms may be configured to tweak or otherwise modify the selected model by also considering minor variations to a promising hypothesis. For example, genetic algorithms may be used to "mate," and "mutate" hypotheses identified as interesting. The final "learned model" may then be used to predict the classification for other objects supplied to the model.

A molecular properties model, however, is of limited usefulness without an estimation of how well it performs. Thus, the accuracy of the model must be estimated. Often, the accuracy of a molecular properties model is calculated using statistical techniques; thus, the accuracy estimate is a random variable, and does not reflect a direct measurement of the actual accuracy for a specific molecular properties model. Thus, simply estimating that a model is 80% accurate is useful only if one has a minimal confidence in the accuracy of the estimate. It is not, however, currently the practice to expend effort estimating or bounding the statistical confidence or higher moments of estimates of model accuracy generated using statistical techniques. In practice, this has led to many molecular properties models with a very high estimated accuracy that, in fact, perform very poorly (i.e., the predictions or classifications prove to be erroneous). Accordingly, there is a need for improved techniques for generating molecular properties models and for estimating and bounding the accuracy and performance of these models or the predictions made using these models.

SUMMARY OF THE INVENTION

Embodiments of the present invention provide methods and apparatus for estimating or bounding the predictive performance of a molecular properties model or molecular properties predictions. There are three major components to this problem and all are addressed by the present invention, they are: defining an appropriate measure of accuracy, estimating the expectation of this accuracy on the population of interest, and estimating or bounding the variance in the estimate of the expectation. Alternative embodiments of the present invention use a variety of novel measures of accuracy for molecular properties models. Given such a measure the present invention provides estimates and bounds on the expectation and higher moments of the accuracy of a molecular properties model using one of three approaches: (i) by using the same data set to both train the model and to estimate the accuracy of the model, (ii) by using distinct data sets to train and subsequently test a model, and (iii) by using multiple models (or sets of predictions).

One embodiment of the invention provides a method for estimating the accuracy of a molecular properties model. The method generally includes, selecting a dataset, wherein the dataset includes at least one molecule description in a form appropriate for the molecular properties model and a value for a molecular property, providing the dataset to the molecular properties model to obtain a prediction for each molecule represented by a molecule description in the dataset, and estimating a confidence interval or bound on the accuracy of the molecular properties model in generating a prediction for a test molecule, based on the predictions generated for the molecules in the dataset, relative to a selected measure of performance.

Another embodiment provides a method for estimating the accuracy of a first molecular properties model trained using a first training dataset. The method generally includes generating a plurality of molecular properties by repeating: (i) modifying the first training dataset to generate a modified dataset, (ii) generating a second molecular properties model corresponding to the modified dataset by performing a selected machine learning algorithm using the modified dataset, (iii) modifying the first training dataset to provide a test dataset to the second molecular properties model, (iv)

obtaining predictions for molecules included in the test dataset, and (v) estimating the accuracy of the second molecular properties model based on the predictions, relative to a selected measure of performance. The method generally further includes estimating a confidence interval or bound on the accuracy of the first molecular properties model in generating a prediction for a test molecule, relative to a selected measure of performance, using the estimates of the accuracy of the plurality of molecular properties models.

In a particular embodiment, the test dataset includes at least one molecule used in training the molecular properties model, and further, may include all of the molecules from the test dataset. Alternatively, the test dataset may be chosen to be maximally different from the data used to train the molecular properties model. Illustrative measures of performance may be selected from the area above an ROC curve, an F-Score, or an Epsilon-insensitive loss. Additionally, the data values for the molecular property may be obtained from experimentation, published data regarding the molecule, or from virtual simulations carried out in silico. Further, embodiments of the invention may be provided as a computer program stored on a computer storage medium which, when executed on a computer system, is configured to perform the methods described herein.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments illustrated by the appended drawings. These drawings, however, illustrate only typical embodiments of the invention and are not limiting of its scope, for the invention may admit to other equally effective embodiments.

DETAILED DESCRIPTION

Figure 1:
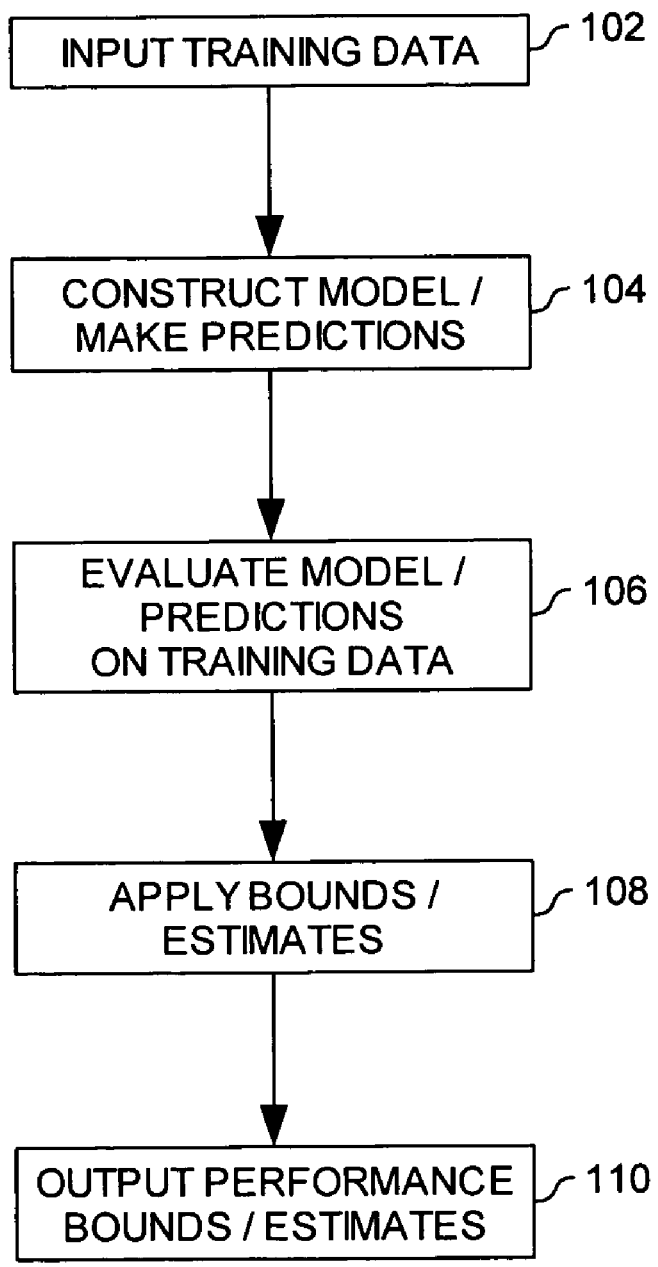
FIG. 1 illustrates a method for estimating the accuracy of a molecular properties model using the same dataset used to train the model and to estimate the accuracy of the model, according to one embodiment of the invention.

Embodiments of the invention may be used to estimate or bound the accuracy of a molecular properties model, or to determine a bound on, or estimate for, the statistical variance inherent in such an accuracy estimate.

In one embodiment, a molecular properties model may be configured to predict an empirically measurable property of a molecule (or atom, bond, molecule substituent, and the like). The property information for a given molecule may be based on intrinsic or extrinsic properties including, for example, pharmacokinetic properties, pharmacodynamic properties, physiological or pharmacological activity, toxicity or selectivity; a chemical property including reactivity, binding affinity, or a property of specific atoms or bonds in a molecule; or a physical property including melting point, solubility, membrane permeability, or a force-field parameter.

Often, the task of the model is to generate a prediction about the property of interest relative to a particular test molecule. Because estimates of model accuracy are based on statistical calculations, embodiments of the invention may be configured to calculate the variance of and theoretical bounds on the accuracy estimated for a given molecular properties model, and further provide techniques to assess the quality of these estimates. Although the three approaches are described separately, those skilled in the art will recognize that embodiments of the invention may merge or combine each of the three approaches to estimate the accuracy of a particular molecular properties model.

Once the accuracy of a given model is estimated, embodiments of the invention may use these estimates in a variety of ways. Illustratively, two examples of how estimates obtained according to the present invention may be used include:

The accuracy estimates of the present invention enable target selection. An in silico molecule discovery or design process may be based on predictive models. Accuracy estimates may be used to determine which models are accurate enough to be used in such a discovery or design process. Hence the availability of such estimates may be used to determine which targets are amenable to in silico molecule discovery or design processes.

Accuracy estimates may be used to determine whether sufficient data is available to train a model and may be used in the determination as to whether more data should be gathered or generated.

Embodiments of the invention estimate the accuracy of a molecular properties model, as described above, according to three general approaches: (i) by using the same data set to both train the model and to estimate the accuracy of the model, (ii) by using distinct data sets to train and subsequently test a model, and (iii) by using multiple models (or sets of predictions).

Further, each of these three approaches may be adapted based on any additional information that may be available. For example, information regarding the distribution of the molecules in the training data or test data, information regarding the difference between the distributions of the training data and test data, and known information regarding the target population may all be used to modify one of these three illustrative approaches.

Although the description herein emphasizes molecular properties models that model properties of whole molecules, this should not be considered limiting of the scope of the present invention. The present invention applies equally to a molecular properties model used to model substituent parts of molecules e.g., atoms, bonds or functional groups and to alternative representations of molecules e.g., alternative 3-dimensional conformations of the molecule. In particular, the invention applies to parameters of molecular mechanics force-fields.

The following description references embodiments of the invention. The invention, however, is not limited to any specifically described embodiment; rather, any combination of the following features and elements, whether related to a described embodiment or not, implements and practices the invention. Moreover, in various embodiments the invention provides numerous advantages over the prior art. Although embodiments of the invention may achieve advantages over other possible solutions and the prior art, whether a particular advantage is achieved by a given embodiment does not limit the scope of the invention. Thus, the following aspects, features, embodiments and advantages are illustrative of the invention and are not considered elements or limitations of the appended claims; except where explicitly recited in a claim. Similarly, references to "the invention" should neither be construed as a generalization of any inventive subject matter disclosed herein nor considered an element or limitation of the appended claims; except where explicitly recited in a claim.

One embodiment of the invention is implemented as a program product for use with a computer system. The program product defines the functions required to perform the methods described herein and may be stored on a variety of computer-readable media. Illustrative computer-readable media include, without limitation, (i) information permanently stored on non-writable storage media (e.g., read-only memory devices within a computer such as CD-ROM disks readable by a CD-ROM drive); (ii) alterable information stored on writable storage media (e.g., floppy disks within a diskette drive or hard-disk drive); and (iii) information conveyed across communications media, (e.g., a computer or telephone network) including wireless communications. The latter embodiment specifically includes information shared over the Internet or other computer networks. Such computer-readable media, when carrying computer-readable instructions that perform methods of the invention, represent embodiments of the present invention.

Furthermore, embodiments of the present invention may be implemented using any form of computer system. Accordingly, the methods described below may be carried out by software configured to execute on systems ranging from single-user workstations, client server networks, large distributed systems employing peer-to-peer techniques, or clustered processing systems wherein multiple CPU's are connected via high-speed networks to function together as a single processing environment.

In general, software routines implementing embodiments of the invention may be part of an operating system or part of a specific application, component, program, module, object, or sequence of instructions such as an executable script. Such software routines comprise a plurality of machine-readable instructions capable of being executed using a computer system. Also, software programs include variables and data structures that reside in memory or on storage devices as part of their operation. In addition, various programs described herein may be identified based upon the application for which they are implemented. Those skilled in the art will recognize, however, that any particular nomenclature or specific application that follows is included to facilitate a description of the invention and does not limit the invention for use solely with a specific application or nomenclature. Furthermore, application programs are described herein using discrete modules or components interacting with one another. Those skilled in the art recognize, however, that different embodiments may combine or merge such components and modules in many different ways.

In one embodiment, molecules (or atoms, molecules, substituent or functional groups, and the like) may be represented using a machine-readable data structure. Generally, as those skilled in the art will recognize, these representations are configured to encode the structure, features, and properties of an atom, bond or molecule that may account for their physical properties. Accordingly, features such as functional groups, steric features, electron density and distribution across a functional group or across the molecule, atoms, bonds, locations of bonds, and other chemical or physical properties of the molecule may be encoded by the representation of a molecule.

Measures of Performance

In order to estimate the accuracy of a molecular properties model, the appropriate definition of accuracy must be explicitly decided. In other words, the measure of performance must be selected, along with a means for quantifying the selected measure. For example, consider a simple classification problem of predicting whether a rock from a mine is a diamond or a lump of coal. One measure of performance is to count all mistakes, whether the mistake is a false positive (i.e., predicting a lump of coal is a diamond) or a false negative (i.e., predicting a diamond is a lump of coal). Accordingly, one way to quantify this measure is to count all mistakes equally. Thus, one accuracy estimate is given by the ratio: (number of correct predictions/total number of predictions). Alternatively, it may be decided that a false negative is much more costly than a false positive. To use the current example, it may be easier to later weed out lumps of coal from a collection of diamonds then to re-evaluate all the discarded objects. Accordingly, an alternative measure of performance would be to greatly penalize false negatives. And estimates of model accuracy may favor models that, in operation, produce fewer false negatives.

As another example, consider a molecular properties model configured to predict the probability of toxicity for a given molecule. Different costs would be associated with incorrect predictions made by such a model, depending on whether the model was predicting that the given molecule would be toxic for laboratory mice versus human beings. Further, such a model may have few costs associated with a false positive, and thus the measure of performance may be selected to disproportionately penalize the false negative molecules.

Embodiments of the invention may use any quantifiable measure of performance. For example, a measure of performance may be selected from at least, classification error, error rate, absolute error, mean squared error, log probability, log likelihood, likelihood, false positive rate, false negative rate, Huber loss, weighted versions of these or arbitrary functions of these, along with other measures of performance whether currently known or later developed.

Embodiments of the present invention may use novel measures of performance for molecular properties models. Specific embodiments of the present invention measure a molecular properties model's ability to rank molecules. In one embodiment this is done by measuring or estimating the area above or below the receiver operator characteristic (ROC) curve (see "Model Selection via the AUC", Saharon Rosset, Proceedings of the $21^{st}$ International Conference on Machine Learning, 2004 incorporated by reference herein in its entirety). The receiver operator characteristic curve applies to models that output a real valued prediction, the ROC curve plots the true positive rate against the false positive rate for the model as a threshold applied to the output is varied. The area above the ROC curve corresponds to a Wilcoxon-Mann-Whitney statistic and is an estimate of the probability that a pair consisting of one active molecule and one inactive molecule is mis-ordered by the model. The area above the ROC curve provides a useful metric when a molecular properties model is used to rank a large set of molecules to select molecules for further study. The area above the ROC curve also provides a useful means to assess the accuracy of a classification model when the trade-off between false-positives and false-negatives is unknown, this is a problem that is poorly addressed by the prior art.

Further embodiments of the present invention use other measures of the ability of a model to rank order molecules with respect to the property of interest. The terms "ranked data" and "rank order" refers to sets of molecules wherein the measurement for the property of interest for one molecule is deemed to be greater (or lesser) than the activity of the other molecules in the set. For example consider the set of two molecules {A, B}, if molecule A has a reported measurement value of 85, and molecule B has a reported measurement value of 70, then molecule A is said to be ranked greater than molecule B. Estimates of such measures are obtained by counting the number of mis-rankings made by the model on some set of data. The estimation procedure may be modified to weight different mis-rankings differently. Further examples of ranking techniques are described in commonly assigned U.S. patent application, filed on even date herewith entitled "Molecular Property Modeling Using Ranking," incorporated by reference herein in its entirety.

Other embodiments of the present invention apply measures of performance used in other fields to the field of molecular properties modeling i.e., F-Score and epsilon-insensitive error. F-score is a measure commonly used in information retrieval applications to trade-off false positives and false negatives, an issue that is poorly addressed by the prior art in molecular properties modeling. Epsilon-insensitive error is a measure that can be used to examine the ability of a molecular properties model to fit a continuous numerical value, it assesses the uniformity of the errors across a large number of molecules, this is an issue that is poorly addressed by the prior art.

Once a measure of performance is selected, embodiments of the invention may estimate or bound the expectation, variance and higher moments of the measure of performance and use these to provide confidence intervals for the accuracy estimate. Embodiments of the invention may also evaluate different hypotheses (i.e., test potential models from a given model-space) against the selected measure of performance and use them to select better or worse performing models.

Using the selected measure of performance, each of the three general approaches may be used to examine the predictive performance of a molecular properties model or predictions generated from such a model.

Estimating Model Accuracy Using Training Data Performance

FIG. 1 illustrates a method 100 for estimating or bounding the accuracy of a molecular properties model for a selected measure of performance, according to one embodiment of the invention. At step 102, a training dataset (including appropriate representations for a selected set of molecules) is input to a selected machine learning algorithm. At step 104, the machine learning algorithm is executed to generate a molecular properties model. At step 106, the "learned model" selected by the machine learning algorithm is used to generate a prediction for the molecules included in the training data. At step 108, bounds and estimates are applied to the predictions generated for the training data, and the resulting bounds or estimates of model performance and accuracy are output at step 110. The bounds or estimates of accuracy for the selected measure of performance may then be applied to any of the typical uses described above.

In one embodiment, the accuracy of a molecular properties model may be estimated using the performance of the model tested against the same dataset used to train the model. The model is applied to the molecules in the training dataset to generate predictions. These predictions together with the known property values for the training molecules are used to estimate a selected measure of performance. For example, if the selected measure of performance is the number of false positives/false negatives that occur, then the false positive/false negative accuracy rates are calculated.

Because the model is the result of an optimization procedure applied to the data being used to estimate its accuracy the resulting estimates will be biased. The present invention accounts for this bias using statistical techniques. Particular embodiments of the present invention apply bounds obtained from the law of large numbers in function space to obtain confidence intervals for the performance of the model. The law of large numbers in function space may be combined with estimates or bounds on the VC-dimension (See "A Result of Vapnik with Applications", Martin Anthony and John Shawe-Taylor, 1991, incorporated by reference herein in its entirety) or statistical complexity of the class of models learned. Furthermore, additional statistics may be obtained from the predictions of the model on the training data e.g., the minimum margin or the distribution of margins. These additional statistics may be combined with VC-dimension, fat-shattering dimension or other statistical complexity measures (see "Structural Risk Minimization over Data-Dependent Hierarchies", Shawe-Taylor, Bartlett, Williamson, and Anthony, IEEE Transactions on Information Theory, 44(5), 1998, incorporated by reference herein in its entirety) to obtain confidence intervals on the performance of the molecular properties models.

In one embodiment, these techniques are used to determine the variance, or theoretical bounds on the variance inherent in the estimate of model accuracy, using, for example, information regarding the complexity of the problem domain, and the power of the model building, machine learning algorithm, or prediction technique, and the like, to bound or estimate the expected performance or accuracy of the model when it is used to generate predictions for molecules not included in the training dataset.

Estimating Model Accuracy Using Test Data Performance

In one embodiment, once a molecular properties model is trained using a first dataset (i.e., the training data), the model is used to generate predictions for molecules represented by a second dataset (i.e., the test data). The second dataset may include molecule representations for a set of molecules that were not included in the training dataset. Alternatively, if the datasets are selected at random (e.g., from a database of candidate molecules) then some overlap may occur.

Figure 2:
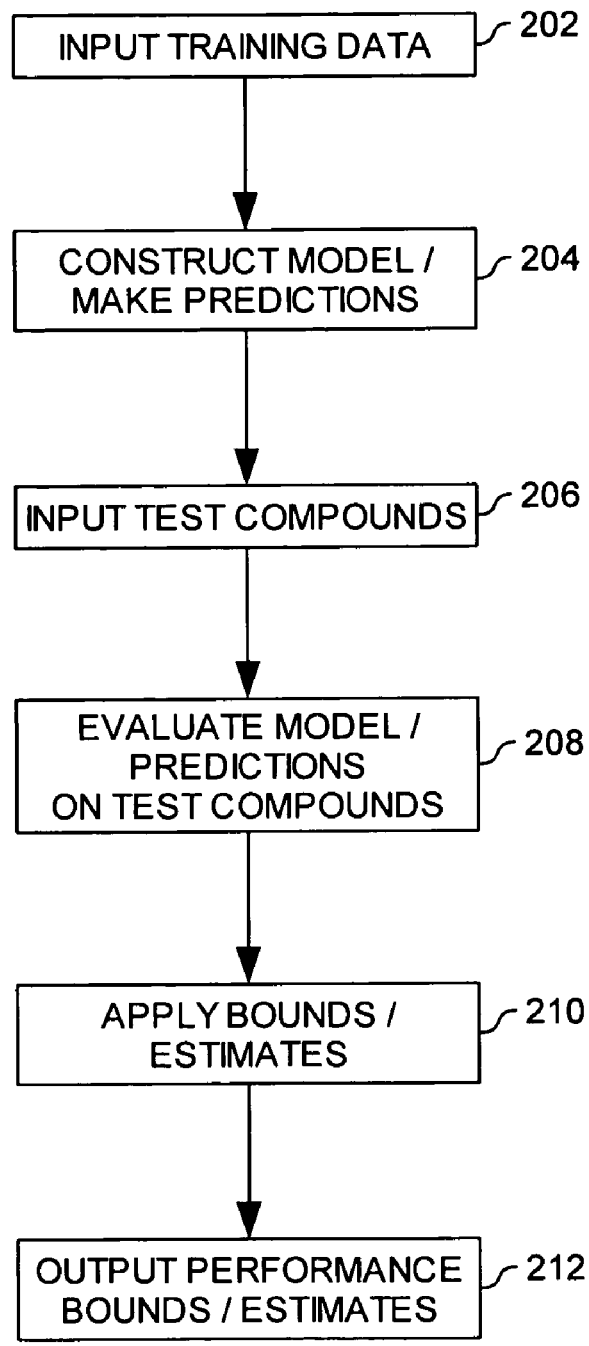
FIG. 2 illustrates a method for estimating the accuracy of a molecular properties model using a dataset of molecules that was not used to train the model, according to one embodiment of the invention.

FIG. 2 is a flow diagram illustrating a method for estimating the accuracy of a molecular properties model using a dataset corresponding to a set of molecules that were not used to train the model, according to one embodiment of the invention. The test dataset and the training dataset may be generated according to any arbitrary division. For example, two sets of molecules may be randomly selected from a database, and the first used to train a molecular properties model, and the second used to test the model. However selected, the models and predictions being generated using the training dataset may be assumed to be approximately independent of the test dataset. At step 202, representations of the training molecules (e.g., the training dataset) are input to a selected machine learning algorithm at step 202. At step 204, the selected machine learning algorithm trains a molecular properties model using the training dataset. The trained model is then used to generate a prediction related to the molecules included in the test dataset. At step 206, a second dataset (i.e., a test dataset) is input to the trained model output during the step 204. At step 208, the model or predictions generated at step 206 are evaluated on the test molecules, relative to the selected measure of performance. At step 210, bounds and estimates are applied to the predictions generated for the test data, and the resulting bounds or estimates of model performance and accuracy are output at step 212. The bounds or estimates of accuracy for the selected measure of performance may then be applied to any of the illustrative uses described above.

In one embodiment of the present invention the test dataset is chosen to be maximally different from the training dataset. Traditionally, in drug discovery, medicinal chemists have used the notion of a scaffold. A scaffold is a family of molecules that are related either by similar 2-dimensional structure or by common synthesis regimens. It is often the case that medicinal chemists desire novel active scaffolds, i.e., scaffolds that contain active molecules that are distinct from previously studied scaffolds. The reasons for this are manifold and include: patentability and ameliorating toxicities. In order to measure a model's ability to "scaffold hop", that is, to accurately predict the activity of molecules in previously unknown scaffolds a diversity splitting technique is disclosed by the present invention. In one embodiment the set of molecules for which data is available is split such that no scaffold is represented in both the training and the testing data. In another embodiment of the present invention some measure of similarity or difference between molecules is used to split the data into two maximally different sets. In another embodiment a knowledgeable expert performs such a partition manually. A variety of techniques may be used to generate two distinct sets of data for training and testing this includes, without limitation, the techniques described above.

Once a model is trained using the training dataset, its accuracy, relative to a selected measure of performance may be generated using the predictions made for the test dataset. Estimates of the accuracy of the model (or of its predictions) may then be determined. For example, methods similar to the ones described above for estimating the accuracy of a molecular properties model using training data may be used. Thus, embodiments of the invention may be configured to generate bounds and estimates of the variance of a model using the independent test dataset. The predictions generated for the test dataset may be used to bound or estimate the performance of the model, when the model is used to generate predictions for molecules that were not included in the training dataset. In particular the expectation of the error on unseen molecules may be well estimated by the empirical expectation of the error on the test dataset. Furthermore, Hoeffding bounds, Chernoff bounds, the Central Limit Theorem or bounds based on McDiarmid's inequality or any other concentration inequality may be used to obtain confidence intervals for the performance of the model. Confidence intervals or estimates of the variance of the model's performance may similarly be measured by estimating them directly from the performance on molecules in the test dataset.

Estimating Model Accuracy Using the Performance of Multiple Models

In another general embodiment, the dataset of molecule representations selected to train a molecular properties model may be modified or sub-sampled to generate multiple models or sets of predictions. The accuracy of the multiple models may then be estimated using the techniques described above. The distribution of the performance of these models or of these predictions is then used to estimate the performance of the final model or predictions, based on the full training dataset.

Figure 3:
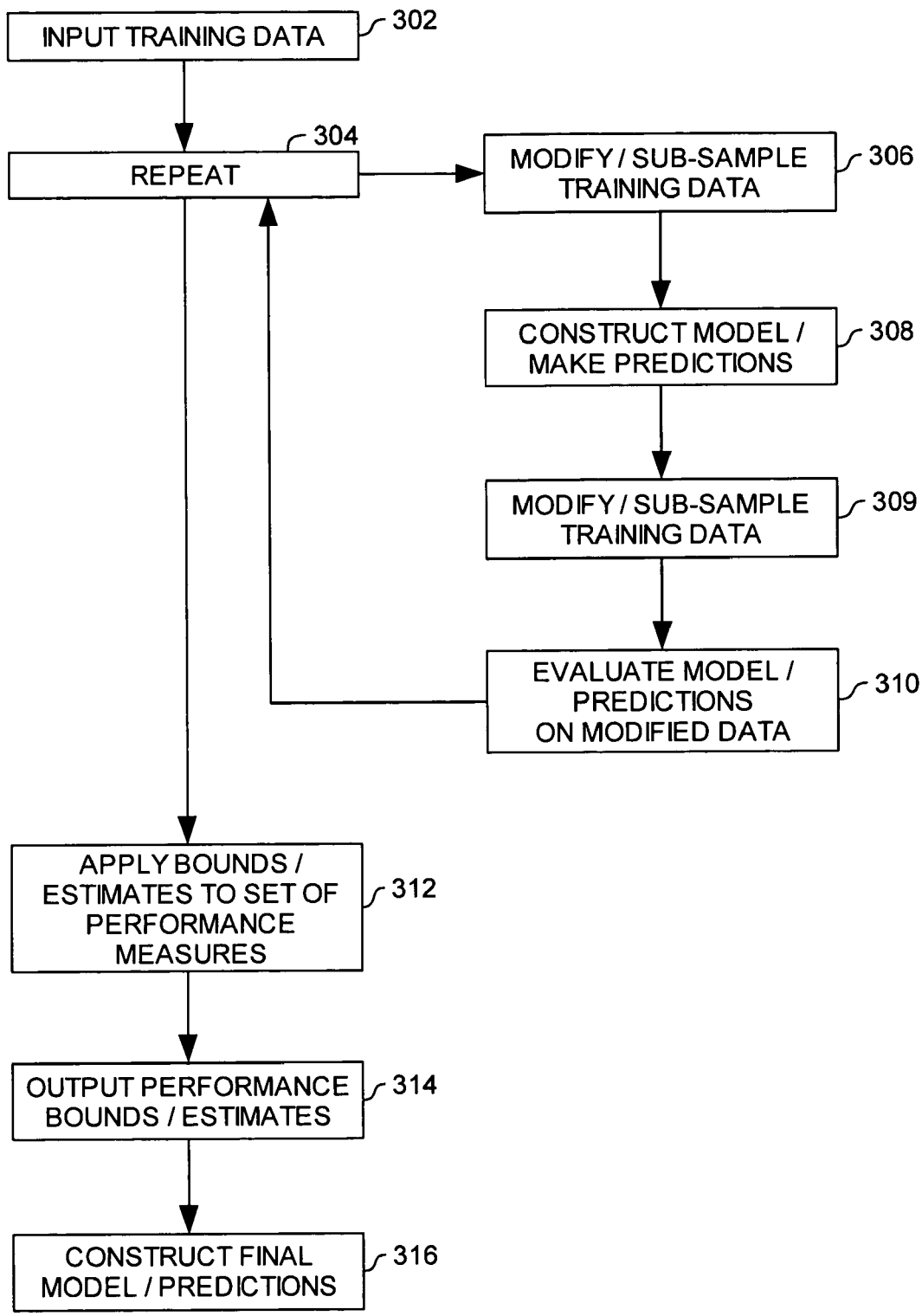
FIG. 3 illustrates a method that may be used to estimate or bound performance of a model (or predictions) by constructing multiple models from a training dataset, according to one embodiment of the invention.

FIG. 3 illustrates a method 300 that may be used to estimate or bound performance of a model (or predictions) by constructing multiple models, according to one embodiment of the invention. At step 302, a training dataset is selected. At step 304, the method 300 enters a loop comprising steps 306, 308, 309, and 310. At step 306, the training dataset is modified or sub-sampled to produce a modified training dataset. At step 308, the modified training dataset produced at step 306 is used by the machine learning algorithm to generate a molecular properties model and to generate a set of predictions using the modified dataset. At step 309, additional modified or sub-sampled training datasets are generated. At step 310, the predictions generated by the models obtained using the modified dataset are evaluated. Repeated iterations of steps 306, 308, 309, and 310 allow the accuracy for a large number of models to be estimated. These estimates for the modified dataset provide an estimate of the accuracy for a molecular properties model trained using the full dataset supplied at step 302. At step 312, bounds and estimates are applied to the predictions generated at step 310, and the resulting bounds or estimates of model performance and accuracy are output at step 314. At step 316, a final model (or predictions) is generated by the selected machine learning algorithm based on the full training dataset, as informed by the data output at step 314.

As those skilled in the art will recognize, often, the more data used to train a model, the better the performance of the resulting model. In one embodiment, once a training dataset is selected, only a portion of the molecules included in the training set is used to actually train a model. For example, the training dataset may be divided into an arbitrary number of partitions. Multiple models may be trained, each using all but one of the partitions as the training data and the remaining partition as the testing data. Because the performance of these models should be only slightly less than the same model trained using the full training dataset, the estimates of the accuracy for each of these models provide estimates on the accuracy of a model trained using the whole set of training data. Furthermore, it provides a distribution of model performance that may be used to estimate the expectation and higher moments of the accuracy of the model, for the selected measure of performance. Thus, although the measure of accuracy may be quite high for a particular model (e.g., because it correctly classifies all of the training data examples), its true performance may be estimated relative to a distribution of models. The accuracy estimates for the multiple models may be obtained using the techniques discussed above based either on performance on the training data used to generate the specific model or on the testing data withheld when learning the specific model.

In one embodiment, instead of partitioning the training dataset (or test dataset) into individual subsets, the training dataset may be repeatedly sub-sampled to select a number of training datasets. The sub-sampling may occur either with or without replacement.

Additionally, embodiments of the invention may sub-sample the training data using a variety of techniques including, without limitation, bootstrapping, k-fold cross-validation, stratified k-fold cross-validation, random sub-sampling, and leave-one-out cross-validation. Embodiments of the invention may also sub-sample the training data to generate diverse splits as discussed above. Multiple sub-samples may be obtained and models are trained on each sub-sample. The performance of each of these models is then estimated using any of the techniques described previously. The resulting estimates and sets of performance measures are then used to bound and estimate the performance of the final model or predictions. In a particular embodiment the multiple estimates of model performance are considered as a distribution of model performance estimates and standard techniques are used to estimate this distribution's mean, variance and higher moments. These estimates of mean and variance are then used to obtain confidence intervals on the true error of the final model trained using all of the data. A variety of techniques may be used to bound or estimate model performance using the estimates of the performance of the multiple models including, without limitation, the techniques described above.

Embodiments of the invention may modify the training data using techniques including permuting the labels or the sample ordering, or randomly re-labeling some or all of the data. This may be done multiple times and models are trained using each of the modified training sets. When re-labeling some or all of the data, one embodiment of the invention measures the performance of each constructed model and uses the resulting set of performance measures or molecular property predictions to estimate the stability, empirical VC-dimension, Rademacher complexity (see "Rademacher and Gaussian Complexities: Risk Bounds and Structural Results", Bartlett and Mendelson, Journal of Machine Learning Research 3, (2002) 463–482 incorporated herein in its entirety) or some other "luckiness" function of the modeling algorithm (see "Measuring the VC-dimension of a learning machine", Vapnik, Levin, and LeCun, Neural Computation 6 (1994) 851–876, incorporated herein in its entirety) on the problem domain. This measure of stability or luckiness can be combined with or used in Hoeffding bounds, Chernoff bounds, the Central Limit Theorem or bounds based on McDiarmid's inequality or any other concentration inequality to obtain bounds on or confidence intervals for the performance of a model trained on the unmodified data.

Incorporation of Additional Knowledge

Using any of the above techniques, or combinations thereof, embodiments of the invention may also incorporate any available additional information to estimate the accuracy of a molecular properties model, relative to the selected measure of performance. For example, when constructing a model, the distributions of data used for the training dataset and testing dataset are often different. Furthermore, these distributions are often different from the distribution on which one is interested in predicting; namely, the target population. Embodiments of the invention address these issues in a number of ways, including, without limitation, diversity splits as described above or sample weighting based on multiplicity or similarity. Further, embodiments of the invention may split the data into sub-samples that are as diverse as possible when performing sub-sampling, bootstrapping or cross-validation or when constructing a test dataset. Thus, similar molecules will not appear in both the training dataset and test dataset. Similarity may be measured using any arbitrary means.

Embodiments of the invention may weight molecules to reduce the exaggerated impact that sets of similar molecules, or molecules that appear a multiplicity of times have in performance measures. This weighting may be performed using arbitrary means.

Use of Virtual Data

The above discussion does not specify the source of testing data. Obtaining such data can be time consuming and prohibitively expensive. Accordingly, embodiments of the present invention may use virtual data obtained from in silico experimentation. Virtual data is described in detail in commonly owned co-pending, U.S. patent application Ser. No. 11/074,587, entitled "Methods for Molecular Property Modeling Using Virtual Data," incorporated herein by reference in its entirety. The property data, for such virtual molecules may be generated based on reasonable assumptions, like those regarding assumed virtual training data described in the 11/074,587 application or from software or hardware applications configured to simulate activity experiments to obtain a measurement value.

Generally, as described in the 11/074,597 application, virtual data is data obtained from sources other than laboratory experiments. Particular embodiments may obtain testing data by performing in silico molecular mechanics or quantum mechanics simulations. Other embodiments may obtain testing data by having an expert manually assign property values to molecules.

Note however, that although the preceding description is with reference to the properties of whole molecules, the invention applies equally to properties of substituents of molecules e.g., atoms, bonds or functional groups or to alternative representations of molecules e.g., alternative feasible 3-dimensional conformations. Examples of such properties include: bond lability, partial charge, aromaticity, force-field parameters, and pKa.

Figure 4:
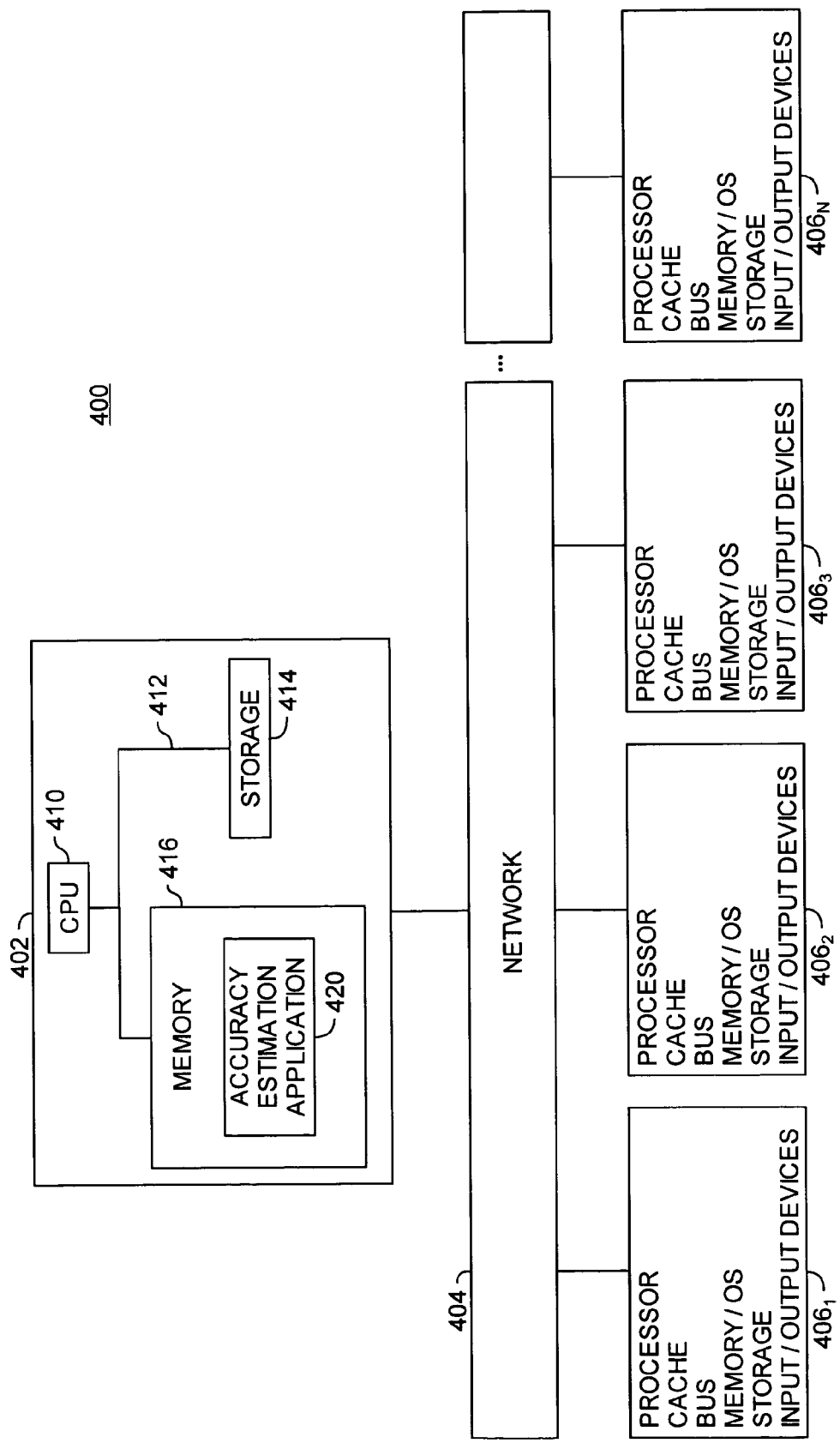
FIG. 4 illustrates an exemplary computing environment 400, according to one embodiment of the invention.

As described above, embodiments of the invention may be implemented as a computer program that may be executed using a computer system. The program (or programs) may be stored using any form of computer storage media. FIG. 4 illustrates an exemplary computing environment 400, according to one embodiment of the invention. Network 404 connects computer system 402 and computer systems, $406_{1-N}$. In one embodiment, computer 402 comprises a server computer system configured to respond to the requests of systems $406_{1-N}$ acting as clients. Computer system 402 generally includes a central processing unit (CPU) 410 connected via a bus 412 to memory 416, storage 414, network interfaces 404, and the like. Illustratively, memory 416 is shown with accuracy estimation software 420 stored therein. Client systems 406 may be similarly configured. Computer systems 402 and $4061_{1-N}$ may also include input/output devices such as a mouse, keyboard, and monitor, and may include other specialized hardware.

Further, the computer systems used to practice the methods of the present invention may be geographically dispersed across local or national boundaries using network 404. Moreover, predictions generated for a test molecule at one location may be transported to other locations using well known data storage and transmission techniques, and predictions may be verified experimentally at the other locations. For example, a computer system may be located in one country and configured to generate predictions about the property of interest for a selected group of molecules, this data may then be transported (or transmitted) to another location, or even another country, where it may be the subject of further investigation e.g., laboratory confirmation of the prediction or further computer-based simulations.

While the foregoing is directed to embodiments of the present invention, other and further embodiments of the invention may be devised without departing from the basic scope thereof, and the scope thereof is determined by the claims that follow.

The invention claimed is:

1. A method for estimating an accuracy of a molecular properties model comprising: selecting a dataset, wherein the dataset includes at least one molecule description in a form appropriate for the molecular properties model and a value for a molecular property; providing the dataset to the molecular properties model to obtain a prediction for each molecule represented by a molecule description in the dataset; and estimating a confidence interval or bound on the accuracy of the molecular properties model in generating a prediction for a test molecule, based on the obtained predictions, relative to a selected measure of performance, wherein the molecular properties model generates predictions related to a property of interest selected from at least one of a physiological activity, pharmacokinetic property, pharmacodynamic property, physiological or pharmacological activity, toxicity or selectivity; a chemical property including reactivity, binding affinity, pKa, or a property of a specific atom or bond in a molecule; or a physical property including melting point, solubility, a membrane permeability, or a force-field parameter.

2. The method of claim 1, wherein the dataset contains at least one molecule description corresponding to a molecule that was also included in a training dataset used to train the molecular properties model.

3. The method of claim 1, wherein the selected measure of performance is selected from at least one of: the area above an ROC curve, and F-Source, or an Epsilon-insensitive loss.

4. The method of claim 1, wherein the value for the molecular property, for at least one molecule description, is generated using an in silico computational simulation.

5. The method of claim 1, wherein concentration inequalities are used to bound the accuracy of the molecular properties model.

6. The method of claim 1, wherein the molecule descriptions are chosen to represent molecules that are maximally different from molecules included in a training dataset used to train the molecular properties model.

7. The method of claim 1, wherein the dataset is chosen to include molecule descriptions representing molecules with different scaffolds than the descriptions representing molecules included in a training dataset used to train the molecular properties.

8. The method of claim 1, wherein the contribution made by the molecule descriptions in the dataset to the molecular properties model are weighted, relative to one another.

9. The method of claim 1, wherein measures of model complexity of "luckiness" functions are used to bound the accuracy of the molecular properties model.

10. The method of claim 1, wherein a calculated variance of the measurements of accuracy on the individual molecule descriptions in the dataset are used to provide a confidence interval for the accuracy of the molecular properties model.

11. A method for estimating the accuracy of a first molecular properties model trained using a first training dataset, comprising:
generating a plurality of molecular properties models by repeating:
(i) modifying the first training dataset to generate a modified training dataset;
(ii) generating a second molecular properties model corresponding to the modified training dataset by performing a selected machine learning algorithm using the modified dataset;
(iii) modifying the first training dataset to provide a test dataset to the second molecular properties model; and
(iv) obtaining predictions for molecules, each represented by a molecule description, included in the test dataset;
(v) estimating the accuracy of the second molecular properties model based on the predictions, relative to a selected measure of performance; and
estimating a confidence interval or bound on the accuracy of the first molecular properties model in generating a prediction for a test molecule, relative to the selected measure of performance, using the estimates of the accuracy of the plurality of molecular properties models.

12. The method of claim 11, wherein the selected measure of performance is selected from at least one of: the area above an ROC curve, and F-Score, or an Epsilon-insensitive loss.

13. The method of claim 11, wherein the value for the molecular property of at least one molecule included in the first training dataset is generated using in silico computational simulation.

14. The method of claim 11, wherein concentration inequalities are used to bound the accuracy of the first molecular properties model.

15. The method of claim 11, wherein the molecules included in the test dataset are chosen to be maximally different from the molecules included in the modified training dataset.

16. The method of claim 11, wherein the test dataset is chosen to include molecules that have different scaffolds than the molecules include in the modified training dataset.

17. The method of claim 11, wherein the first molecular properties model generates predictions related to a property, of interest selected from at least one of a physiological or pharmacological activity, toxicity or selectivity; a chemical property including reactivity, binding affinity, pka, or a property of a specific atom or bond in a molecule; or a physical property including melting point, solubility, a membrane permeability, of a force-field parameter.

18. The method of claim 11, wherein the contribution made by the molecule descriptions in the dataset to the molecular properties model are weighted, relative to one another.

19. The method of claim 11, wherein measures of model complexity or "luckiness" functions are used to bound the accuracy of the first molecular properties model.

20. The method of claim 11, wherein the variance of the measurements of accuracy on the plurality of molecular properties models is used to provide a confidence interval regarding the accuracy of the first molecular properties model.

21. The method of claim 11, wherein the first training dataset is modified by selecting reduced sets of molecules by cross-validation, stratified cross-validation bootstrapping, sub-sampling, or leave-one-out.

22. The method of claim 11, wherein the first training dataset is modified at step i by changing or permuting the values for the molecular property.

23. The method of claim 11, wherein the plurality of molecular properties models is used to estimate the empirical VC-dimension, the Rademacher complexity, or another empirical estimate of the complexity of the model class from which the first molecular properties model is selected.

24. A computer-readable medium containing a program which, when executed by a processor, performs operations comprising: receiving a dataset, wherein the dataset includes at least one molecule description in a form appropriate for the molecular properties model and a value for a molecular property; providing the dataset to the molecular properties model to obtain a prediction for each molecule represented by a molecule description in the dataset; and estimating a confidence interval or bound on the accuracy of the molecular properties model in generating a prediction for a test molecule, based on the obtained predictions, relative to a selected measure of performance, wherein the molecular properties model generates predictions related to a property of interest selected from at least one of a physiological activity, pharmacokinetic property, pharmacodynamic property, physiological or pharmacological activity, toxicity or selectivity; a chemical property including reactivity, binding affinity, pKa, or a property of a specific atom or bond in a molecule; or a physical property including melting point, solubility, a membrane permeability, or a force-field parameter.

25. The computer-readable medium of claim 24, wherein the dataset contains at least one molecule description corresponding to a molecule that was also included in a training dataset used to train the molecular properties model.

26. The computer-readable medium of claim 24, wherein the molecule descriptions are chosen to represent molecules that are maximally different from molecules included in a training dataset used to train the molecular properties model.

27. The computer-readable medium of claim 24, wherein the selected measure of performance is selected from at least one of: the area above an ROC curve, an F-Score, or an Epsilon-insensitive loss.

28. The computer-readable medium of claim 24, wherein the value for the molecular property for at least one molecule description in the dataset is generated using an in silico computational simulation.

29. The computer-readable medium of claim 24, wherein the dataset is chosen to include molecule descriptions representing molecules with different scaffolds than the descriptions representing molecules included in a training dataset, used to train the molecular properties model.

30. A computer-readable medium containing a program which, when executed by a processor, performs operations for estimating the accuracy of a first molecular properties model trained using a first training dataset comprising generating a plurality of molecular properties models by repeating:
(i) modifying the first training dataset to generate a modified training dataset;
(ii) generating a second molecular properties model corresponding to the modified training dataset by performing a selected machine learning algorithm using the modified dataset;
(iii) modifying the first training dataset to provide a test dataset to the second molecular properties model; and
(iv) obtaining predictions for molecules, each represented by a molecule description, included in the test dataset;
(v) estimating the accuracy of the second molecular properties model based on the predictions, relative to a selected measure of performance; and estimating a confidence interval or bound on the accuracy of the first molecular properties model in generating a prediction for a test molecule, relative to the selected measure of performance, using the estimates of the accuracy of the plurality of molecular properties models.

31. The computer-readable medium of claim 30, wherein the first training dataset is modified by selecting reduced sets of molecules by cross-validation, stratified cross-validation, bootstrapping, sub-sampling, or leave-one-out.

32. The computer-readable medium of claim 30, wherein the first training dataset is modified at step i by changing or permuting the values for the molecular property.

33. The computer-readable medium of claim 30, wherein the plurality of molecular properties models is used to estimate the empirical VC-dimension, the Rademacher complexity, or another empirical estimate of the complexity of the model class from which the first molecular properties model is selected.

* * * * *

UNITED STATES PATENT AND TRADEMARK OFFICE
CERTIFICATE OF CORRECTION

PATENT NO. : 7,194,359 B2 Page 1 of 1
APPLICATION NO. : 11/172216
DATED : March 20, 2007
INVENTOR(S) : Nigel P. Duffy et al.

It is certified that error appears in the above-identified patent and that said Letters Patent is hereby corrected as shown below:

Column 12, Line 43 change "$4061_{1-N}$" to --$406_{1-N}$--.

Column 13, Line 25 change "F-Source," to --F-Score,--.

Column 13, Line 42 after "molecular properties" add --model--.

Column 14, Lines 32-33 change "property, of interest" to --property of interest--.

Column 14, Line 35 change "pka, or" to --pKa, or"--.

Column 14, Line 33 after "at least one of a" insert --physiological activity, pharmacokinetic property, pharmacodynamic property,--.

Signed and Sealed this

Twentieth Day of May, 2008

JON W. DUDAS
*Director of the United States Patent and Trademark Office*